United States Patent
Van Hout et al.

(10) Patent No.: US 10,308,042 B2
(45) Date of Patent: Jun. 4, 2019

(54) RADIATION-CURABLE INKJET INK COMPOSITION

(71) Applicant: Océ Holding B.V., Venlo (NL)

(72) Inventors: Richard F. E. Van Hout, Venlo (NL); Björn H. A. J. M. Ketelaars, Venlo (NL); R. Van Hameren, Venlo (NL); Bas Venderbosch, Venlo (NL)

(73) Assignee: OCÉ HOLDING B. V., Venlo (NL)

( * ) Notice: Subject to any disclaimer, the term of this patent is extended or adjusted under 35 U.S.C. 154(b) by 139 days.

(21) Appl. No.: 15/460,695

(22) Filed: Mar. 16, 2017

(65) Prior Publication Data

US 2017/0283640 A1    Oct. 5, 2017

(30) Foreign Application Priority Data

Mar. 30, 2016  (EP) ..................... 16162733

(51) Int. Cl.
| | |
|---|---|
| *B41J 11/00* | (2006.01) |
| *C09D 11/34* | (2014.01) |
| *C07C 69/76* | (2006.01) |
| *C09D 11/101* | (2014.01) |
| *C09D 11/107* | (2014.01) |

(Continued)

(52) U.S. Cl.
CPC ............ *B41J 11/002* (2013.01); *C07C 69/76* (2013.01); *C09D 11/101* (2013.01); *C09D 11/107* (2013.01); *C09D 11/34* (2013.01); *C09D 11/38* (2013.01); *C09D 11/40* (2013.01)

(58) Field of Classification Search
CPC ... B41J 2/01; B41J 2/211; B41J 2/1433; B41J 2/17; B41J 2/17593; B41J 2/2107; B41J 2/1755; B41J 2/2114; B41J 2/2117; B41J 2/2056; B41J 2/21; B41J 2/0057; B41J 3/60; B41J 2002/012; B41J 2/04598; B41J 2/04588; B41J 2/04595; B41J 2/04586; B41J 2/14274; B41J 11/0015; B41J 11/002; B41J 2/161; B41J 2/1623; B41J 2202/00; B41J 2202/03; B41J 2/14201; B41J 2/045; C09D 11/36; C09D 11/40; C09D 11/30; C09D 11/38; C09D 11/32; C09D 11/322; C09D 11/324; C09D 11/328; C09D 11/101; C09D 11/102; C09D 11/005; C09D 11/54; C09D 11/52; B41M 5/0011; B41M 5/0017; B41M 5/0047; B41M 7/00; B41M 7/0072; B41M 5/52; B41M 5/5218
See application file for complete search history.

(56) References Cited

U.S. PATENT DOCUMENTS

2005/0287476 A1*  12/2005  Ishikawa ............... C09D 11/101
                                                                         430/281.1
2007/0076071 A1   4/2007   Iu et al.
(Continued)

OTHER PUBLICATIONS

Search Report for European Patent Application No. 16162733.6, completed on Sep. 19, 2016.

*Primary Examiner* — Manish S Shah
(74) *Attorney, Agent, or Firm* — Birch, Stewart, Kolasch & Birch, LLP

(57) ABSTRACT

The present invention relates to a radiation curable ink composition including a gellant. The present invention further relates to an ink set having such ink composition. The present invention further relates to a method for making such ink composition and a printing method using such ink composition.

8 Claims, 2 Drawing Sheets

(51) Int. Cl.
  *C09D 11/38* (2014.01)
  *C09D 11/40* (2014.01)

(56) References Cited

U.S. PATENT DOCUMENTS

| | | |
|---|---|---|
| 2008/0081119 A1* | 4/2008 | Oyanagi .............. C09D 11/101 |
| | | 106/31.13 |
| 2008/0122914 A1* | 5/2008 | Toma .................. C09D 11/101 |
| | | 347/100 |
| 2011/0262711 A1 | 10/2011 | Chopra et al. |
| 2012/0040287 A1 | 2/2012 | Wang et al. |
| 2012/0157562 A1 | 6/2012 | Chopra et al. |
| 2012/0282448 A1 | 11/2012 | Chretien et al. |

\* cited by examiner

RADIATION-CURABLE INKJET INK COMPOSITION

The present invention relates to an ink composition and to an ink set comprising such ink composition. The present invention further relates to a method for preparing an ink composition. In addition, the present invention relates to a method for applying an image onto a recording medium.

BACKGROUND OF THE INVENTION

Radiation-curable inkjet ink compositions are known in the art. These ink compositions comprise one or more radiation-curable components. A special class of radiation-curable inkjet ink compositions are phase change radiation-curable inkjet ink compositions. These inks are fluid at elevated temperature and become solid—even if not yet cured—at lower temperatures. These inks are typically jetted at elevated temperatures. Phase change inks may become solid or semi-solid upon cooling down on a recording medium, e.g. a sheet of paper. As a result, spread of a droplet of ink on the recording medium may be decreased and color bleeding may be prevented. An example of a phase change radiation-curable inkjet ink is a gelling radiation-curable inkjet ink. Gelling radiation-curable inkjet ink compositions typically comprise a gellant. Gellants are also known in the art as gelling agents or thickeners. Examples of gellants used in gelling radiation curable inkjet ink compositions are waxes, such as natural waxes and long chain carboxylic acids, and ketones. The presence of a gellant can cause a viscosity increase in the inkjet ink composition upon cooling of the ink composition. The viscosity increase in the ink composition should be sufficient, to adequately control droplet spreading. The use of a gelling may allow to postpone curing of the ink after applying the ink onto the recording medium.

A disadvantage of gelling inks is that liquid components may diffuse from the gelled phase to unprinted parts of the recording medium, which may result in the formation of transparent zone around the droplet. This phenomenon is called halo. Halo formation decreases the image quality of a printed image. There is a need for gelling radiation curable ink compositions that do not show halo.

It is therefore an object of the present invention to provide a gelling radiation curable ink composition that does not show halo.

SUMMARY OF THE INVENTION

The object of the invention is achieved in a radiation-curable inkjet ink composition, wherein the gellant is a compound according to formula I,

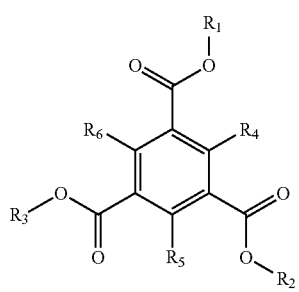

formula I wherein $R_1$, $R_2$ and $R_3$ are each independently selected from an alkyl, an arylalkyl, an alkenyl group and a $R'(OCH_2CHR'')_x(OCH_2CHR''')_y(OCH_2CHR'''')_z$— group, wherein R' is an alkyl group having 1-4 carbon atoms, R'', R''' and R'''' are each independently selected from a hydrogen atom, a methyl group or an ethyl group and x, y, z are integers in the range of 0-20, wherein x+y+z is in the range of 4-30 and wherein $R_4$, $R_5$ and $R_6$ are each independently selected from a hydrogen atom and an alkyl group having 1-4 carbon atoms.

Radiation-Curable Medium

The radiation-curable inkjet ink composition may comprise a radiation-curable medium. The radiation-curable medium may comprise at least one radiation-curable component. A radiation-curable component is a component that may react (e.g. polymerize) under influence of suitable radiation, such as electromagnetic radiation, e.g. ultraviolet (UV) radiation. Examples of radiation-curable components are epoxides and (meth)acrylates. (Meth-)acrylates may comprise one or more reactive groups for forming an acrylate polymer. The radiation-curable medium may comprise one type of radiation curable compound or alternatively, the radiation-curable medium may comprise a mixture of radiation-curable compounds.

The radiation-curable medium may further comprise at least one inhibitor. An inhibitor is a component that prevent (inhibits) unwanted polymerization of the radiation-curable compound. Inhibitors may be added to the radiation curable inkjet ink composition to increase the shelf life of the ink composition.

The radiation-curable medium may further comprise at least one photo initiator. A photo initiator is a component that improves the efficiency of curing; i.e. increases the polymerization rate when the ink composition is irradiated with suitable radiation, such as UV radiation.

The radiation-curable medium may further comprise a solvent, such as water or an organic solvent. The solvent may be added to the radiation curable medium to tune ink properties, such as viscosity.

Further, additional components may be added to the radiation curable medium. For example, the radiation curable medium may comprise surfactants, antibacterial components and anti-fungi components.

Colorant

The radiation curable inkjet ink composition may further comprise a colorant, such as a pigment, a dye or a mixture thereof. Further, the radiation curable inkjet ink composition may comprise a mixture of dyes and/or a mixture of pigments. The colorant may provide the ink composition with a predetermined color.

Gellant

The radiation-curable inkjet ink composition may further comprise a gellant. According to the present invention the gellant is a compound according to formula

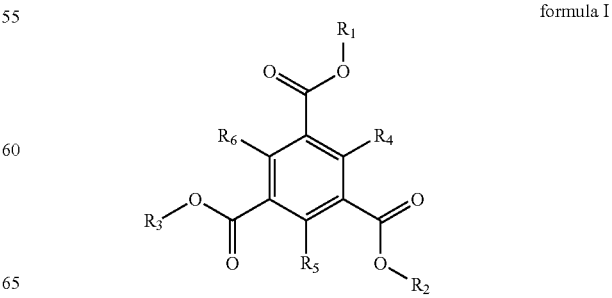

formula I wherein $R_1$, $R_2$ and $R_3$ are each independently selected from an alkyl, an arylalkyl, an alkenyl group and a R'(OCH$_2$CHR")$_x$(OCH$_2$CHR''')$_y$(OCH$_2$CHR"")$_z$— group, wherein R' is an alkyl group having 1-4 carbon atoms, R", R''' and R"" are each independently selected from a hydrogen atom, a methyl group or an ethyl group and x, y, z are integers in the range of 0-20, wherein x+y+z is in the range of 4-30 and wherein $R_4$, $R_5$ and $R_6$ are each independently selected from a hydrogen atom and an alkyl group having 1-4 carbon atoms.

Preferably, $R_1$, $R_2$ and $R_3$ each may be independently selected from an alkyl group, an alkenyl group or an alkylarylgroup. When any of the functional group $R_1$, $R_2$ and $R_3$ comprises an aromatic unit, then pi-pi-interaction may occur. Pi-pi interaction may assist in forming the intermolecular network upon cooling of the ink composition comprising the ester compound, which may be beneficial for the increase in viscosity of the ink composition when cooling down.

Each one of the group $R_1$, $R_2$ and $R_3$ may be a group comprising 5-40 carbon atoms, preferably 10-25. When two or more of the functional groups $R_1$, $R_2$ and $R_3$ comprise less than 5 carbon atoms, then the compound may not show gelling behavior at printing conditions. When any of the functional groups $R_1$, $R_2$ and $R_3$ comprises more than 40 carbon atoms, then the viscosity of the ink composition comprising this compound may be too high at jetting conditions, which may hamper the jetting of the inkjet ink composition. The compound may comprise only one type of functional group $R_1$, $R_2$ and $R_3$. Alternatively, the compound may comprise a plurality of different functional groups $R_1$, $R_2$ and $R_3$.

It was found that radiation-curable inks comprising such gellant may prevent halo formation and are therefore suitable to print images having high image quality.

In an embodiment, $R_4$, $R_5$ and $R_6$ each represent a hydrogen atom. Compounds according to formula I, wherein $R_4$, $R_5$ and $R_6$ each represent a hydrogen atom are also referred to as 1,3,5-benzenetricarboxylates.

In an embodiment, $R_1$, $R_2$ and $R_3$ are each independently selected from an alkyl group having 8-25 carbon atoms. Components according to formula I, wherein $R_1$, $R_2$ and $R_3$ are each a long chain alkyl group, e.g. an alkyl group comprising 8-25 carbon atoms provide good gelling properties. When forming a network in a fluid ink vehicle, the long chain alkyl groups may interact via so-called Van der Waals forces, which may increase the strength of the gelled network. The length of the alkyl chains may influence the properties of the gellant, which may influence i.e. the gelling temperature, which is the temperature below which a gel is formed. The optimal chain length may depend e.g. on the parameters of the printing process and the nature of the radiation-curable inkjet ink composition.

In a further embodiment, $R_1$, $R_2$ and $R_3$ are the same. In such case, the symmetry of the gellant molecule is increased, which may increase the strength of the intermolecular forces between gellant molecules. The stronger the intermolecular forces between gellant molecules, the stronger the gel formed.

In a further embodiment, $R_4$, $R_5$ and $R_6$ each represent a hydrogen atom and $R_1$, $R_2$ and $R_3$ are the same and each represent a long chain alkyl.

For example $R_1$, $R_2$ and $R_3$ may each represent a dodecyl group. In that case, the name of the gellant is: tridodecyl-1,3,5-benzenetricarboxylate. In another example, $R_1$, $R_2$ and $R_3$ may each represent a tetradecyl group (tritetradecyl-1,3,5-benzenetricarboxylate). Alternatively, $R_1$, $R_2$ and $R_3$ may each represent a hexadecyl group (trihexadecyl-1,3,5-benzenetricarboxylate). In a further alternative, $R_1$, $R_2$ and $R_3$ may each represent a octadecyl group (trioctadecyl-1,3,5-benzenetricarboxylate).

In an embodiment, the gellant is present in an amount of 0.2 wt %-3.0 wt % based on the total weight of the radiation-curable inkjet ink composition. For example, the gellant may be present in an amount of 0.5 wt %-2.5 wt % based on the total weight of the radiation-curable inkjet ink composition, such as from 1.0 wt %-2.0 wt % based on the total weight of the radiation-curable inkjet ink composition.

It was surprisingly found that a small amount of the gellant in accordance with the present invention may suffice to efficiently increase the viscosity of the radiation curable inkjet ink composition in between jetting of a droplet onto a recording medium and curing of the ink by irradiation.

Gellants may form three dimensional structures below a gelling temperature. Hence, when the inkjet ink composition is gelled, a three dimensional structure of the gellant may form in the inkjet ink composition. Such three dimensional structure may comprise crystals. The presence of crystals may decrease the gloss level of a print made using the inkjet ink composition. Therefore, decrease of the gloss level may be prevented by using only small amounts of gellant, for example 0.2 wt %-3.0 wt % based on the total weight of the radiation-curable inkjet ink composition.

In an embodiment, the radiation curable component is an acrylate having two or more acrylate functional groups. An acrylate may undergo a polymerization reaction when irradiated by suitable radiation, such as UV radiation. Hence, a polyacrylate polymer may be formed when an inkjet ink composition comprising an acrylate is cured, thereby hardening the ink. An acrylate molecule having two or more acrylate functional groups may react with two or more other acrylate molecules and hence, a polymeric network may be formed. Examples of acrylates having two or more acrylate functional groups are known in the art.

In a further embodiment, the ink composition further comprises a monofunctional acrylate. Presence of a monofunctional acrylate may improve the hardness and flexibility of the ink layer after curing.

In an embodiment, an ink set is provided, wherein the ink set comprises a radiation-curable inkjet ink composition according to the present invention.

An ink set may comprise a plurality of different inks. For example, the ink set may be a CMYK ink set, comprising a Yellow, a Magenta, a Cyan and a blacK ink composition. At least one of the ink compositions in the ink set may be an ink comprising a gellant, wherein the gellant is a compound according to formula I as described above. Preferably, a plurality of the ink compositions in the ink set may comprise a gellant, wherein the gellant is a compound according to formula I as described above. The ink set may further comprise additional colors, such as white, red, green, light magenta, light cyan and/or grey. Further, the ink set may comprise one or more metallic ink compositions. Optionally, the ink set may comprise an undercoat and/or an overcoat composition. The undercoat and/or overcoat composition may be colorless ink compositions.

An ink set, wherein at least one of the inkjet ink compositions comprises a gellant in accordance with the present invention may allow printing images free of halo.

In an aspect of the invention, use of a component according to formula I in a radiation-curable inkjet ink composition is provided,

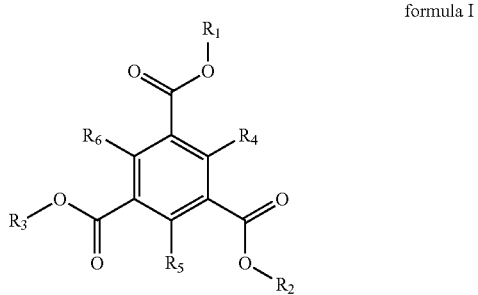

formula I wherein $R_1$, $R_2$ and $R_3$ are each independently selected from an alkyl, an arylalkyl, an alkenyl group and a $R'(OCH_2CHR'')_x(OCH_2CHR''')_y(OCH_2CHR'''')_z-$ group, wherein R' is an alkyl group having 1-4 carbon atoms, R", R''' and R'''' are each independently selected from a hydrogen atom, a methyl group or an ethyl group and x, y, z are integers in the range of 0-20, wherein x+y+z is in the range of 4-30 and wherein $R_4$, $R_5$ and $R_6$ are each independently selected from a hydrogen atom and an alkyl group having 1-4 carbon atoms.

Such component may be suitably used in radiation-curable inkjet ink composition as a gellant.

In an aspect of the invention, a method for preparing a radiation-curable inkjet ink composition is provided, the method comprising the steps of:
  providing a radiation-curable component;
  providing gellant, wherein the gellant is a compound according to formula I,

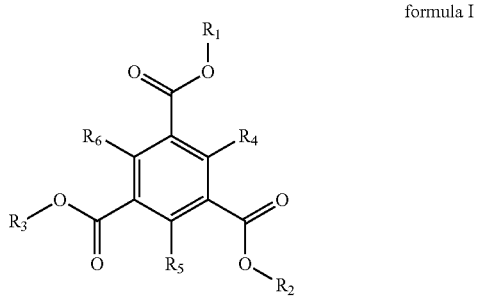

formula I wherein $R_1$, $R_2$ and $R_3$ are each independently selected from an alkyl, an arylalkyl, an alkenyl group and a $R'(OCH_2CHR'')_x(OCH_2CHR''')_y(OCH_2CHR'''')_z-$ group, wherein R' is an alkyl group having 1-4 carbon atoms, R", R''' and R'''' are each independently selected from a hydrogen atom, a methyl group or an ethyl group and x, y, z are integers in the range of 0-20, wherein x+y+z is in the range of 4-30 and wherein $R_4$, $R_5$ and $R_6$ are each independently selected from a hydrogen atom and an alkyl group having 1-4 carbon atoms;
  mixing the radiation curable component and the gellant.

The radiation-curable component and the gellant may be provided. Optionally, additional components may be provided, for example an additional solvent. The radiation-curable component and the gellant may be provided neat or they may be provided in a solution or dispersion. Optionally, a colorant may be provided. In case the colorant is a pigment, the pigment is preferably provided as a dispersion, such as an aqueous pigment dispersion. The components may be provided at once, or the components may be added subsequently. The components may be added in any suitable order. In case a dispersible component is added (e.g. a pigment), such dispersible component may be preferably added after the other components of the ink composition are provided. Mixing of the components may be carried out at any suitable temperature, for example room temperature.

In an aspect of the invention, a method for applying an image onto a recording medium is provided, the method comprising the steps of:
  a. jetting droplets of a radiation-curable inkjet ink composition according to the present invention onto the recording medium;
  b. curing the radiation-curable inkjet ink composition by irradiating the ink composition using UV radiation.

In the method, an image is applied onto a recording medium. In the method, in step a), an image is applied to the recording medium. The image may be applied using an ink composition according to the present invention. The ink composition may be applied onto the recording medium in a predetermined fashion, e.g. in accordance with image files stored on suitable storing means. The image may be applied for example by jetting droplets of the radiation-curable inkjet ink composition using an inkjet print head. The recording medium may be a sheet-like medium, such as a sheet of paper or a sheet of vinyl. Alternatively, the recording medium may be a web, for example an endless belt. The web may be made of a suitable material. Optionally, the image may be dried after it has been applied onto the intermediate transfer member.

In the method, in step b), the radiation-curable inkjet ink composition is cured by irradiating the ink composition using UV radiation. The inkjet ink composition may be irradiated using a suitable source of radiation, such as a halogen lamp, a mercury lamp and/or a LED lamp. Optionally, a plurality of sources of radiation may be used to irradiate the inkjet ink composition.

BRIEF DESCRIPTION OF THE DRAWINGS

These and further features and advantages of the present invention are explained hereinafter with reference to the accompanying drawings showing non-limiting embodiments and wherein.

In the drawings, same reference numerals refer to same elements.

DETAILED DESCRIPTION OF THE DRAWINGS

Figure 1A:
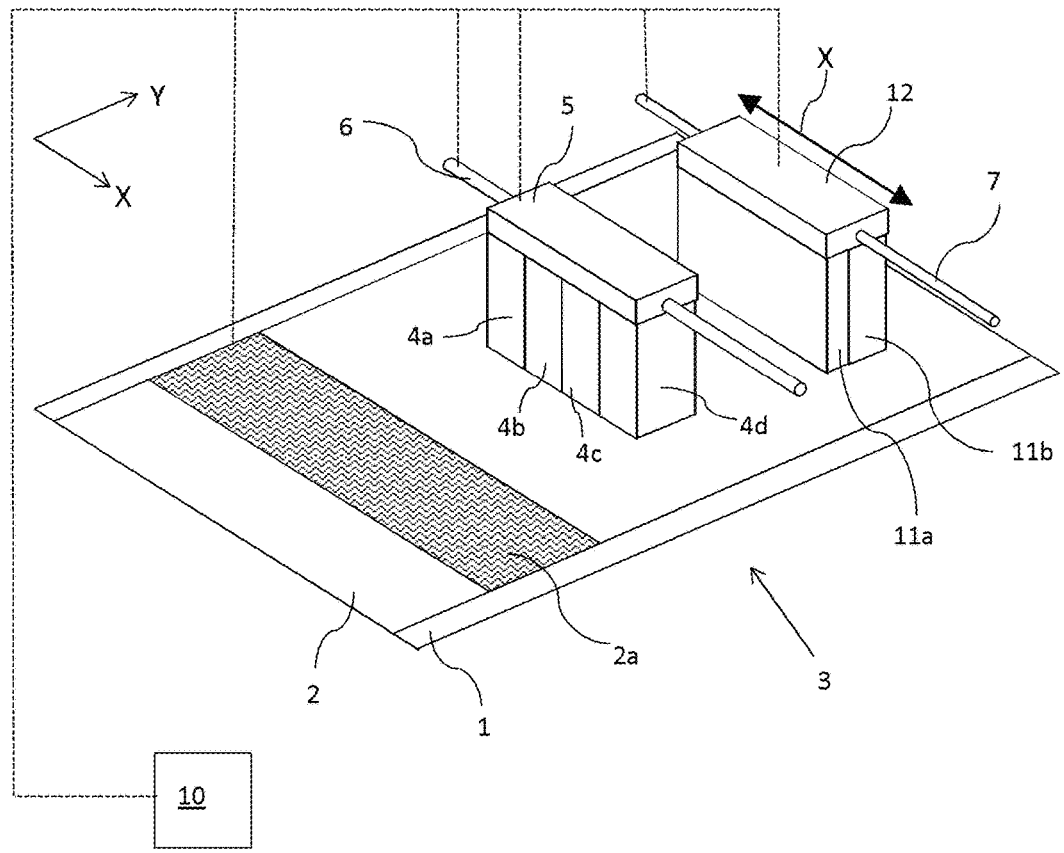
FIG. 1A shows a schematic representation of an inkjet printing system.
Figure 1B:
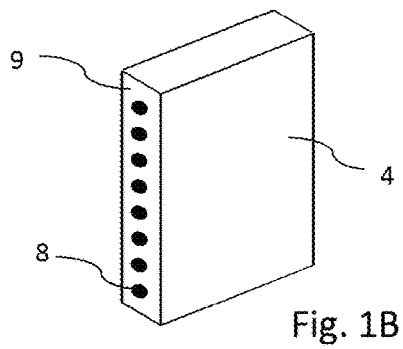
FIG. 1B shows a schematic representation of an inkjet print head.

FIG. 1A shows an ink jet printing assembly 3. The ink jet printing assembly 3 comprises supporting means for supporting an image receiving medium 2. The supporting means are shown in FIG. 1A as a flat surface 1, but alternatively, the supporting means may be a platen, for example a rotatable drum that is rotatable around an axis. The supporting means may be optionally provided with suction holes for holding the image receiving medium in a fixed position with respect to the supporting means. The ink jet printing assembly 3 comprises print heads 4a-4d, mounted on a scanning print carriage 5. The scanning print carriage 5 is guided by suitable guiding means 6 to move in reciprocation in the main scanning direction X. Each print head 4*a*-4*d* comprises an orifice surface 9, which orifice surface 9 is provided with at least one orifice 8, as is shown in FIG. 1B. The print heads 4*a*-4*d* are configured to eject droplets of marking material onto the image receiving medium 2.

The image receiving medium 2 may be a medium in web or in sheet form and may be composed of e.g. paper, cardboard, label stock, coated paper, plastic or textile. Alternatively, the image receiving medium 2 may also be an intermediate member, endless or not. Examples of endless members, which may be moved cyclically, are a belt or a drum. The image receiving medium 2 is moved in the sub-scanning direction Y over the flat surface 1 along four print heads 4*a*-4*d* provided with a fluid marking material.

The image receiving medium 2, as depicted in FIG. 1A is locally heated or cooled in the temperature control region 2*a*. In the temperature control region 2A, temperature control means (not shown), such as heating and/or cooling means may be provided to control the temperature of the receiving medium 2. Optionally, the temperature control means may be integrated in the supporting means for supporting an image receiving medium 2. The temperature control means may be electrical temperature control means. The temperature control means may use a cooling and/or heating liquid to control the temperature of the image receiving medium 2. The temperature control means may further comprise a sensor (not shown) for monitoring the temperature of the image receiving medium 2.

A scanning print carriage 5 carries the four print heads 4*a*-4*d* and may be moved in reciprocation in the main scanning direction X parallel to the platen 1, such as to enable scanning of the image receiving medium 2 in the main scanning direction X. Only four print heads 4*a*-4*d* are depicted for demonstrating the invention. In practice an arbitrary number of print heads may be employed. In any case, at least one print head 4*a*-4*d* per color of marking material is placed on the scanning print carriage 5. For example, for a black-and-white printer, at least one print head 4*a*-4*d*, usually containing black marking material is present. Alternatively, a black-and-white printer may comprise a white marking material, which is to be applied on a black image-receiving medium 2. For a full-color printer, containing multiple colors, at least one print head 4*a*-4*d* for each of the colors, usually black, cyan, magenta and yellow is present. Often, in a full-color printer, black marking material is used more frequently in comparison to differently colored marking material. Therefore, more print heads 4*a*-4*d* containing black marking material may be provided on the scanning print carriage 5 compared to print heads 4*a*-4*d* containing marking material in any of the other colors. Alternatively, the print head 4*a*-4*d* containing black marking material may be larger than any of the print heads 4*a*-4*d*, containing a differently colored marking material.

The carriage 5 is guided by guiding means 6. These guiding means 6 may be a rod as depicted in FIG. 1A. Although only one rod 6 is depicted in FIG. 1A, a plurality of rods may be used to guide the carriage 5 carrying the print heads 4. The rod may be driven by suitable driving means (not shown). Alternatively, the carriage 5 may be guided by other guiding means, such as an arm being able to move the carriage 5. Another alternative is to move the image receiving material 2 in the main scanning direction X.

Each print head 4*a*-4*d* comprises an orifice surface 9 having at least one orifice 8, in fluid communication with a pressure chamber containing fluid marking material provided in the print head 4*a*-4*d*. On the orifice surface 9, a number of orifices 8 are arranged in a single linear array parallel to the sub-scanning direction Y, as is shown in FIG. 1B. Alternatively, the nozzles may be arranged in the main scanning direction X. Eight orifices 8 per print head 4*a*-4*d* are depicted in FIG. 1B, however obviously in a practical embodiment several hundreds of orifices 8 may be provided per print head 4*a*-4*d*, optionally arranged in multiple arrays.

As depicted in FIG. 1A, the respective print heads 4*a*-4*d* are placed parallel to each other. The print heads 4*a*-4*d* may be placed such that corresponding orifices 8 of the respective print heads 4*a*-4*d* are positioned in-line in the main scanning direction X. This means that a line of image dots in the main scanning direction X may be formed by selectively activating up to four orifices 8, each of them being part of a different print head 4*a*-4*d*. This parallel positioning of the print heads 4*a*-4*d* with corresponding in-line placement of the orifices 8 is advantageous to increase productivity and/or improve print quality. Alternatively multiple print heads 4*a*-4*d* may be placed on the print carriage adjacent to each other such that the orifices 8 of the respective print heads 4*a*-4*d* are positioned in a staggered configuration instead of in-line. For instance, this may be done to increase the print resolution or to enlarge the effective print area, which may be addressed in a single scan in the main scanning direction X. The image dots are formed by ejecting droplets of marking material from the orifices 8.

The ink jet printing assembly 3 may further comprise curing means 11*a*, 11*b*. As shown in FIG. 1A, a scanning print carriage 12 carries the two curing means 11*a*, 11*b* and may be moved in reciprocation in the main scanning direction X parallel to the platen 1, such as to enable scanning of the image receiving medium 2 in the main scanning direction X. Alternatively, more than two curing means may be applied. It is also possible to apply page-wide curing means. If page-wide curing means are provided, then it may not be necessary to move the curing means in reciprocation in the main scanning direction X. The first curing means 11*a* may emit a first beam of UV radiation, the first beam having a first intensity. The first curing means 11*a* may be configured to provide the radiation for the pre-curing step. The second curing means 11*b* may emit a second beam of radiation, the second beam of radiation having a second intensity. The second curing means 11*b* may be configured to provide the radiation for the post-curing step.

The carriage 12 is guided by guiding means 7. These guiding means 7 may be a rod as depicted in FIG. 1A. Although only one rod 7 is depicted in FIG. 1A, a plurality of rods may be used to guide the carriage 12 carrying the print heads 11. The rod 7 may be driven by suitable driving means (not shown). Alternatively, the carriage 12 may be guided by other guiding means, such as an arm being able to move the carriage 12.

The curing means may be energy sources, such as actinic radiation sources, accelerated particle sources or heaters. Examples of actinic radiation sources are UV radiation sources or visible light sources. UV radiation sources are preferred, because they are particularly suited to cure UV curable inks by inducing a polymerization reaction in such inks. Examples of suitable sources of such radiation are lamps, such as mercury lamps, xenon lamps, carbon arc lamps, tungsten filaments lamps, light emitting diodes (LED's) and lasers. In the embodiment shown in FIG. 1A, the first curing means 11*a* and the second curing means 11*b* are positioned parallel to one another in the sub scanning direction Y. The first curing means 11*a* and the second curing means 11*b* may be the same type of energy source or may be different type of energy source. For example, when the first and second curing means 11a, 11b, respectively both emit actinic radiation, the wavelength of the radiated emitted by the two respective curing means 11a, 11b may differ or may be the same. The first and second curing means are depicted as distinct devices. However, alternatively, only one source of UV radiation emitting a spectrum of radiation may be used, together with at least two distinct filters. Each filter may absorb a part of the spectrum, thereby providing two beams of radiation, each one having intensity different from the other.

The flat surface 1, the temperature control means, the carriage 5, the print heads 4a-4d, the carriage 12 and the first and second curing means 11a, 11b are controlled by suitable controlling means 10.

EXPERIMENTS AND EXAMPLES

Materials

SR 9003 (propoxylated neopentyl glycol diacrylate) was obtained from Sartomer. Tegorad 2250 was obtained from Evonik. Stearone was obtained from KAO under the tradename KAOwax T-1. Irgacure 819 was obtained from BASF. All chemicals were used as received. MPI2000, which was obtained from Avery Denison was used as recording medium.

The synthesis of trihexadecyl-1,3,5-benzenetricarboxylate is described below.

Methods

Image Formation

Image formation samples were prepared by applying a droplet of ink onto a recording medium. 60 Seconds after the droplet was applied onto the recording medium, the droplet was cured by irradiating with a LED emitting 395 nm radiation. The droplet was irradiated until it was fully cured.

The image formation samples obtained were inspected using an optical microscope.

Example 1

27.44 grams of hexadecan-1-ol (117 mmol, 3.1 eq.) was dissolved into heptane (150 mL) by heating the solution to 50° C. To the solution 9.99 grams of 1,3,5-benzenetricarbonyl trichloride (37.7 mmol, 1 eq.) was added. After 15 minutes, 9.5 mL pyridine (117 mmol, 3.1 eq.) was added to the reaction mixture. After 30 minutes, the formed pyridine hydrochloride salt was filtrated from the solution and the solution was cooled to 0° C., to crystallize the reaction product. The reaction product was filtrated from the solution and dried over vacuum to yield trihexadecyl 1,3,5-benzenetricarboxylate (compound A, 16.76 grams, 44% yield).

Ink Example and Comparative Ink Example

Two colorless ink compositions were prepared.

A first ink composition was prepared by putting together 1 gram of compound A, 93.9 gram of SR 9003, 5 gram of Irgacure 819 and 0.1 gram of Tegorad 2250 and mixing the components. This first ink composition is an ink composition according to the present invention and will be referred to as Ex 1.

A second ink composition was prepared by putting together 1 gram of KAOwax T-1, 93.9 gram of SR 9003, 5 gram of Irgacure 819 and 0.1 gram of Tegorad 2250 and mixing the components. This second ink composition is not an ink composition according to the present invention and will be referred to as CE1.

Comparison Experiments.

Figure 2A:
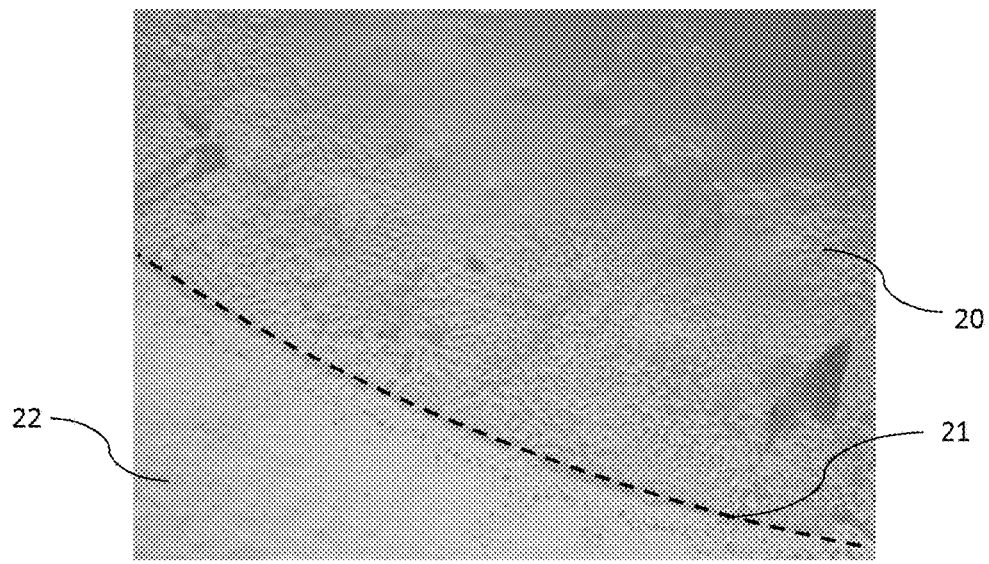
FIG. 2A shows a print example according to an embodiment of the present invention.

Two image formation samples were prepared. A first image formation sample was prepared by applying a droplet of ink composition Ex 1 onto the recording medium. A part of this image formation sample is shown in FIG. 2A. In FIG. 2A, a part of the droplet 20 is shown. Further, a part of the recording medium not covered by ink 22 is observed. The droplet 20 has an outer periphery 21. The outer periphery 21 forms the border between the cured ink droplet 21 and the recording medium not covered by ink 22. No halo is observed in FIG. 2A.

Figure 2B:
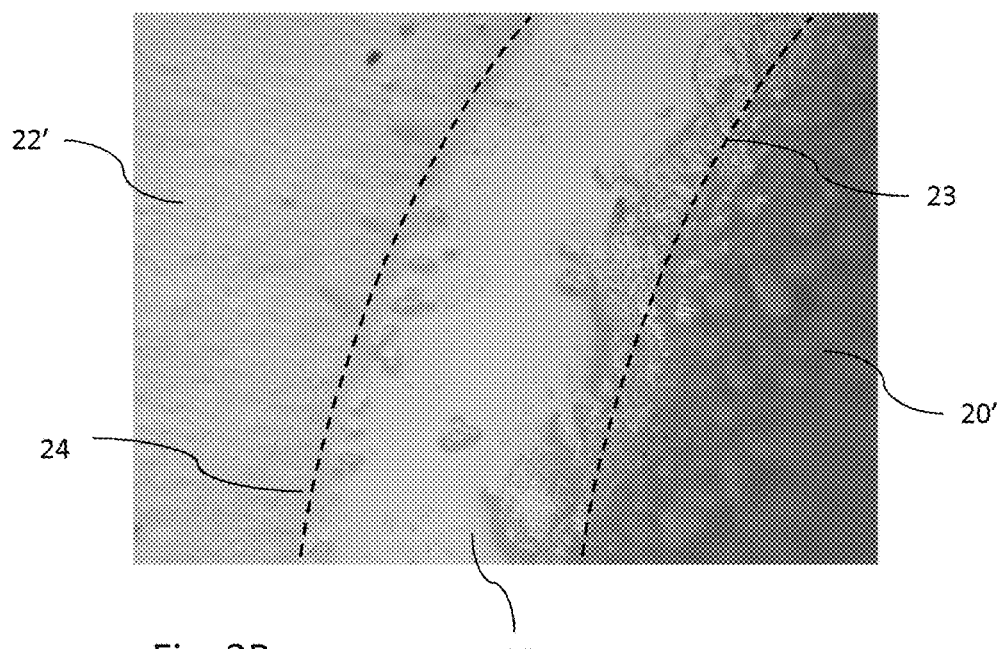
FIG. 2B shows a print example not according to the present invention.

A second image formation sample was prepared by applying a droplet of ink composition CE 1 onto the recording medium. A part of this image formation sample is shown in FIG. 2B. In FIG. 2B, a part of the droplet 20' is shown. Further, a part of the recording medium not covered by ink 22' is observed. Unlike the sample shown in FIG. 2A, in the sample shown in FIG. 2B, a transparent layer 25 is observed in between the droplet 20' and the recording medium not covered by the ink 22'. This transparent layer 25 is a so-called halo. The droplet as shown in FIG. 2B has an outer periphery 23. This outer periphery 23 forms a border between the (cured) ink droplet and the transparent layer 25 forming the halo. The transparent layer 25 also has an outer periphery 24, which forms the border between the transparent layer and the recording medium not covered by ink 22'.

Thus, in the image formation sample made with ink composition CE 1, which is not an ink composition according to the present invention shows halo, whereas the image formation sample made with ink composition Ex 1, which is an ink composition according to the present invention does not show halo. Thus, when using an ink composition according to the present invention, halo formation can be prevented.

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually and appropriately detailed structure. In particular, features presented and described in separate dependent claims may be applied in combination and any combination of such claims are herewith disclosed. Further, the terms and phrases used herein are not intended to be limiting; but rather, to provide an understandable description of the invention. The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly.

The invention claimed is:

1. Radiation-curable inkjet ink composition comprising a gellant, wherein the gellant is a compound according to formula I,

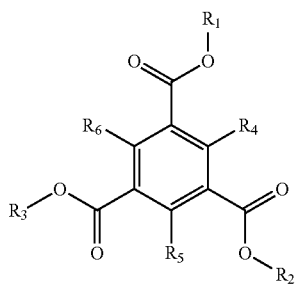

formula I wherein $R_1$, $R_2$ and $R_3$ are each independently selected from an alkyl, an arylalkyl, an alkenyl group and a R'(OCH$_2$CHR")$_x$(OCH$_2$CHR''')$_y$(OCH$_2$CHR'''')$_z$— group,
wherein R' is an alkyl group having 1-4 carbon atoms, R", R''' and R'''' are each independently selected from a hydrogen atom, a methyl group or an ethyl group and x, y, z are integers in the range of 0-20, wherein x+y+z is in the range of 4-30 and wherein $R_4$, $R_5$ and $R_6$ are each independently selected from a hydrogen atom and an alkyl group having 1-4 carbon atoms.

2. Radiation-curable inkjet ink composition according to claim 1, wherein $R_4$, $R_5$ and $R_6$ each represent a hydrogen atom.

3. Radiation-curable inkjet ink composition according to claim 1, wherein $R_1$, $R_2$ and $R_3$ are each independently selected from an alkyl group having 8-25 carbon atoms.

4. Radiation-curable inkjet ink composition according to claim 3, wherein $R_1$, $R_2$ and $R_3$ are the same.

5. Radiation-curable inkjet ink composition according to claim 1, wherein the gellant is present in an amount of 0.2 wt %-3.0 wt % based on the total weight of the radiation-curable inkjet ink composition.

6. Radiation-curable inkjet ink composition according to claim 1, wherein the ink composition comprises an acrylate having two or more acrylate functional groups.

7. Radiation-curable inkjet ink composition according to claim 6, wherein the ink composition further comprises a monofunctional acrylate.

8. Ink set comprising a radiation-curable inkjet ink composition according to claim 1.

* * * * *